US012758286B2

(12) United States Patent
Andermatt et al.

(10) Patent No.: US 12,758,286 B2
(45) Date of Patent: Oct. 13, 2026

(54) DEVICE TO ALIGN THE ANGLE OR A DISTANCE OF A BONE FIXATION PLATE

(71) Applicant: DePuy Synthes Products, Inc., Raynham, MA (US)

(72) Inventors: Daniel Andermatt, Möhlin (CH); This Aebi, Solothurn (CH); Dirk Kerstan, Biberstein (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 19/227,791

(22) Filed: Jun. 4, 2025

(65) Prior Publication Data

US 2025/0380974 A1 Dec. 18, 2025

Related U.S. Application Data

(60) Provisional application No. 63/657,345, filed on Jun. 7, 2024.

(51) Int. Cl.
*A61B 17/80* (2006.01)
*A61B 90/00* (2016.01)

(52) U.S. Cl.
CPC ........ *A61B 17/808* (2013.01); *A61B 17/8061* (2013.01); *A61B 2090/067* (2016.02)

(58) Field of Classification Search
CPC ... A61B 17/80; A61B 17/808; A61B 17/8061; A61B 17/17; A61B 17/1728; A61B 17/1757; A61B 90/06; A61B 90/11
See application file for complete search history.

(56) References Cited

U.S. PATENT DOCUMENTS

| | | | | |
|---|---|---|---|---|
| 6,796,986 B2 * | 9/2004 | Duffner | A61B 17/15 606/86 R |
| 8,323,292 B2 * | 12/2012 | Dudasik | A61B 17/025 606/105 |
| 11,589,877 B2 * | 2/2023 | Duerr | A61B 17/152 |
| 11,896,243 B2 * | 2/2024 | Aoude | A61B 17/1757 |
| 2018/0125549 A1 * | 5/2018 | Gradl | A61B 17/8061 |

FOREIGN PATENT DOCUMENTS

| | | |
|---|---|---|
| CN | 103054641 B | 4/2015 |
| CN | 111166455 A | 5/2020 |
| CN | 114469373 B | 8/2023 |

OTHER PUBLICATIONS

Roebke, et al., "Lift-Off Screw Results in Accurate Sagittal Tilt Correction in a Distal Radius Fracture Model", Journal of Hand Surgery (American Volume), vol. 43, Jun. 2018, 6 pages.

* cited by examiner

*Primary Examiner* — Christopher J Beccia
(74) *Attorney, Agent, or Firm* — Flaster Greenberg P.C.

(57) ABSTRACT

A device may be configured to convert an angle to a distance to assist with securing a bone fixation plate during a surgical procedure. The device may include a body. The body may include (e.g., define) an elongated first portion and/or a second portion. The elongated first portion may include at least one aperture. The at least one aperture may be configured to receive a wire and/or a screw. The second portion may include angular indicia. The device may include an arm. The arm may be rotatably coupled, for example to the body. Additionally, or alternatively, the arm may be rotatably coupled at a rotation point.

20 Claims, 18 Drawing Sheets

1300

Conversion sheet (one chart for all Plates/Hole distances)

| | Plate A Hole 1 | Plate A Hole 2 | Plate A Hole 3 | Hole 4 |
|---|---|---|---|---|
| Angle [°] | H1 [mm] | H2 [mm] | H3 [mm] | H4 [mm] |
| 10 | 6 | 9 | 10 | 12 |
| 15 | 10 | 13 | 15 | 18 |
| 20 | 13 | 18 | 21 | 24 |
| 25 | 17 | 23 | 27 | 31 |
| 30 | 21 | 28 | 33 | 39 |
| 35 | 25 | 34 | 40 | 47 |
| 40 | 30 | 41 | 48 | 56 |
| 45 | 36 | 49 | 57 | 67 |

DEVICE TO ALIGN THE ANGLE OR A DISTANCE OF A BONE FIXATION PLATE

CROSS-REFERENCE TO RELATED APPLICATIONS

This application claims the benefit of U.S. Provisional Application No. 63/657,345 filed on Jun. 7, 2024, the entire contents of which are incorporated herein by reference.

BACKGROUND

In a medical context, systems for alignment of bones in an operative procedure may useful, especially in wrist surgery. For example, systems may be useful to restore alignment of bones in a volar plate osteosynthesis procedure.

Existing solutions may result in insufficient alignment. For example, there may be insufficient correction of volar tile post-fixation using current systems. Additionally, residual sagittal plane malalignment has been shown to alter ulnocarpal contact forces and joint kinematics, leading to suboptimal outcomes, especially in young and high-demand patients.

SUMMARY

The application is generally related to devices and methods used for alignment of surfaces, for example in a medical context, and more particularly, to alignment of bones in an operative procedure. In some examples, the devices described herein can be used to assist a with the alignment of a bone fixation plate during a surgical procedure.

A device may be configured to convert an angle to a distance. The device may include a body. The body may include (e.g., define) an elongated first portion and/or a second portion. The elongated first portion may include at least one aperture. The at least one aperture may be configured to receive a wire and/or a screw. The second portion may include angular indicia.

The device may include an arm. The arm may be rotatably coupled, for example to the body. Additionally, or alternatively, the arm may be rotatably coupled at a rotation point. The device may include a rod. The rod may be coupled to the arm, for example at the rotation point. The rod may be configured to rotate about the rotation point, for example with rotation of the arm. The arm may be configured to align with an angular indicia of the second portion of the body, for example to indicate an angle. Additionally, or alternatively, the arm may be configured to align with the angular indicia when the rod is aligned to be parallel with a plane. The arm may be configured to indicate a distance to the at least one aperture of the first portion of the body, for example when the rod is a line to be parallel with the plane and/or the arm is aligned with the angular indicia to indicate an angle.

The distance may indicate a depth of a screw and/or a wire. A screw may be for screwing a plate onto a patient, for example at a wrist of the patient. The distance may additionally, or alternatively, indicate a depth that the wire can extend through the aperture, for example when a wire is used to position a bone fixation plate for screwing onto the wrist of the patient. The distance may be associated with a corrective open reduction and internal fixation alignment, for example a corrective distance.

The plane may include a tangent line, for example drawn along a slope of a dorsal to palmer surface (e.g., of a wrist of the patient). The arm may include a marker. The marker may be configured to align with the angular indicia of the second portion of the body. The elongated first portion may include a first lip. The at least one aperture may be disposed in the first lip. The arm may comprise a second lip. The second lip may be configured to abut the wire. The at least one aperture may include at least three apertures. The three apertures may include an H2 aperture, an H3 aperture, and an H4 aperture. The H2, H3, and H4 apertures may be referred to as hole 2, hole 3, and hole 4 respectively. One or more of the apertures, for example the H2, H3, and/or H4 apertures, may be notches. Each of the at least three apertures may correspond to a respective aperture on a bone fixation plate. For example, H2 (e.g., 408), H3 (e.g., 409), and H4 (e.g., 411) of the device may correspond to respective holes H2 (e.g., 210), H3 (e.g., 212), and H4 (e.g., 214) of a bone fixation plate. Angular indicia may indicate a value of 0, for example when the arm is in contact with the elongated first portion.

A device may include a guide tube. The guide tube may define a hollow interior. The hollow interior may be configured to receive a wire, for example such that the wire can extend through the guide tube. The device may include a clamping sleeve. The clamping sleeve may be disposed around the circumference of the guide tube. The clamping sleeve may be configured to receive the wire and/or restrict motion of the wire through the guide tube, for example when in a first configuration. The clamping sleeve may be configured to allow movement of the wire through the guide tube, for example when in a second configuration.

The clamping sleeve may include a hole and/or an actuator. An interior surface of the hole may be configured to contact the wire, for example when the wire is extending through the hole to restrict the motion of the wire through the guide tube (e.g., in the first configuration). The actuator may be configured to be actuated to cause the hole to separate from the wire, for example to allow movement of the wire through the guide tube (e.g., in the second configuration). The actuator and/or the hole may be disposed in a plane. The plane may be perpendicular to an axis associated with the motion of the wire. The clamping sleeve may include at least one clip. The at least one clip may be configured to at least partially enclose the guide tube.

The clamping sleeve may include an elongated aperture. The elongated aperture may receive the wire therethrough. The elongated aperture may include a first end and a second end. The clamping sleeve may include a plurality of flexible members. The plurality of flexible members may extend from the second end of the elongated aperture. The plurality of flexible members may contact the wire, for example when the clamping sleeve is coupled to the guide tube.

The plurality of flexible members may include (e.g., each include) threading, for example at a distal end. The guide tube may include threading, for example such that the clamping sleeve may screw into the guide tube. The plurality of flexible members may flex inward, for example to contact the wire when the clamping sleeve is screwed into the guide tube (e.g., in the second configuration). The guide tube may include threading, for example such that the guide tube may thread into a bone fixation plate. The guide tube may include a window. The window may display a value indicative of a length of the wire extending from an end of the guide tube.

Additional features and advantages are realized through the system of the present invention. Other embodiments and aspects of the disclosure are described in detail herein. For a better understanding of the disclosure with advantages and features, refer to the description and to the drawings.

BRIEF DESCRIPTION OF THE DRAWINGS

Many aspects of the disclosure can be better understood with reference to the following drawings. The components in the drawings are not necessarily to scale, with emphasis being placed upon clearly illustrating the principles of the present disclosure. Moreover, in the drawings, like reference numerals designate corresponding parts throughout the several views. Furthermore, each drawing contained in this provisional application includes at least a brief description thereon and associated text labels further describing associated details.

DETAILED DESCRIPTION

Herein, example embodiments of the present disclosure will be described in detail. Example embodiments of the present disclosure provide a systems and methods. Systems and methods may be used for alignment of surfaces, for example in a medical context, and more particularly, to alignment of bones in an operative procedure when attaching a bone fixation plate to a patient. The operative procedure may correct a fracture, for example a distal radius fracture.

A distal radius fracture may be dorsally angulated. A corrective (e.g., operative) procedure may be performed. Operative management of a corrective procedure, for example a desired volar tilt, may utilize one or more indications for operative fixation. An indication may include a post-reduction intra-articular displacement, for example greater than 2 mm. Another example indication may include a radial shortening, for example greater than 3 mm. Yet another indication may include a dorsal tilt, for example greater than 10°. Operative management as herein may be utilized to achieve articular reduction. Additionally, or alternatively operative management may be utilized to restore a volar tilt to a normal anatomic volar tilt of the distal radius. An operative procedure may be a distal first procedure. The distal first procedure may include fixation of a distal fragment (e.g., closer to the wrist) before the proximal fragment (e.g., closer to the elbow).

Operative management may include a volar plate osteosynthesis procedure. However, complete restoration of desired volar tilt may be challenging, for example in a dorsally angulated fracture pattern with metaphyseal comminution. There may be insufficient correction of volar tilt post-fixation with current systems and procedures. For example, residual sagittal plane malalignment has been shown to alter ulnocarpal contact forces and joint kinematics leading to suboptimal outcomes, for example in young and/or high-demand patients.

Systems and methods as herein may achieve accurate and consistent alignment of bones in an operative procedure, for example in wrist surgery. For example, a system may restore the desired volar tilt in a controlled fashion. The system may include controlled lifting of a plate, for example from the radius. The plate may include one or more screws (e.g., locking screws), for example with a selected (e.g., user selected) length. Additionally, or alternatively, a spacer may assist in achieving accurate alignment.

Figure 1A:
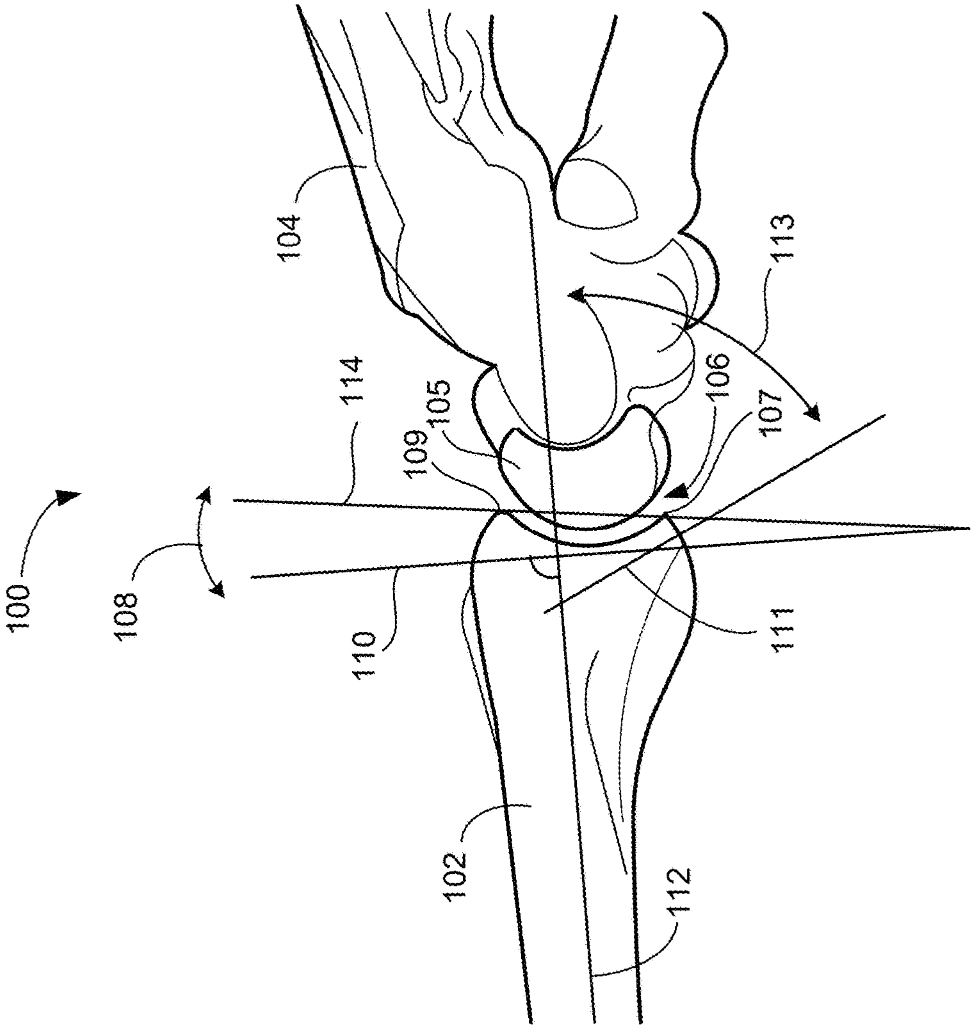
FIG. 1A is a view of an example joint of a patient.

FIG. 1A is a view of an example joint 100 of a patient. A bone 102 may connect to a hand 104, for example at one or more carpals 105. The bone 102 may be a radius. The bone may connect to the one or more carpals 105 at a joint 106. The joint 106 may be a radiocarpal joint. The bone 102 may include an axis 112, for example extending through an elongated portion of the bone 102. A line 110 may be perpendicular to the axis 112.

There may be a first point 107 and a second point 109, for example of the bone 102. The first point 107 and the second point 109 may be boundaries of a dorsal to palmar surface. A tangent line 114 may be along a slope of the dorsal to palmar surface. The tangent line 114 may be defined such that the tangent line 114 contacts the first point 107 and the second point 109. The tangent line 114 may extend, at least partially, through the joint 106 and/or the one or more carpals 105.

A volar tilt angle 108 may be defined between the line 110 and the tangent line 114. The volar tilt angle 108 may include the angle between the line 110 and the tangent line 114. The bone 102 (e.g., radius) may include a radial shaft 111. A teardrop angle 113 may be defined between the radial shaft 111 and the axis 112. A normal teardrop angle is 67-69 degrees.

Figure 1B:
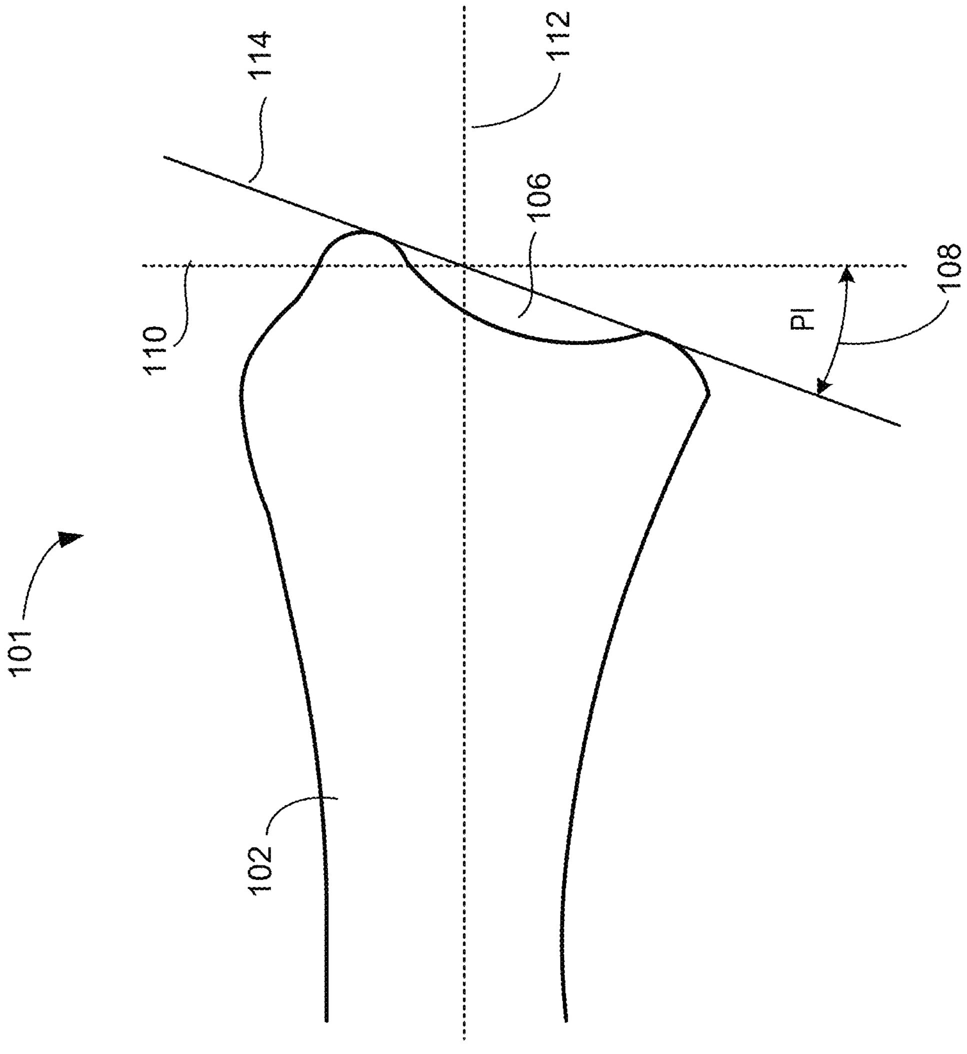
FIG. 1B is a view of an example joint of a patient with a palmar angle.

FIG. 1B is a view of an example joint 101 of a patient with a volar tilt angle 108. The volar tile angle may also be referred to as a palmar angle. FIG. 1B shows the volar tilt angle 108 as the angle between the axis 112 of the bone (e.g., radius) and the line 110 perpendicular to the axis 112. A normal volar tilt angle 108 is 10-25 degrees. A desired volar tilt angle 108 after an operative procedure may be approximately 10 degrees.

Figure 2:
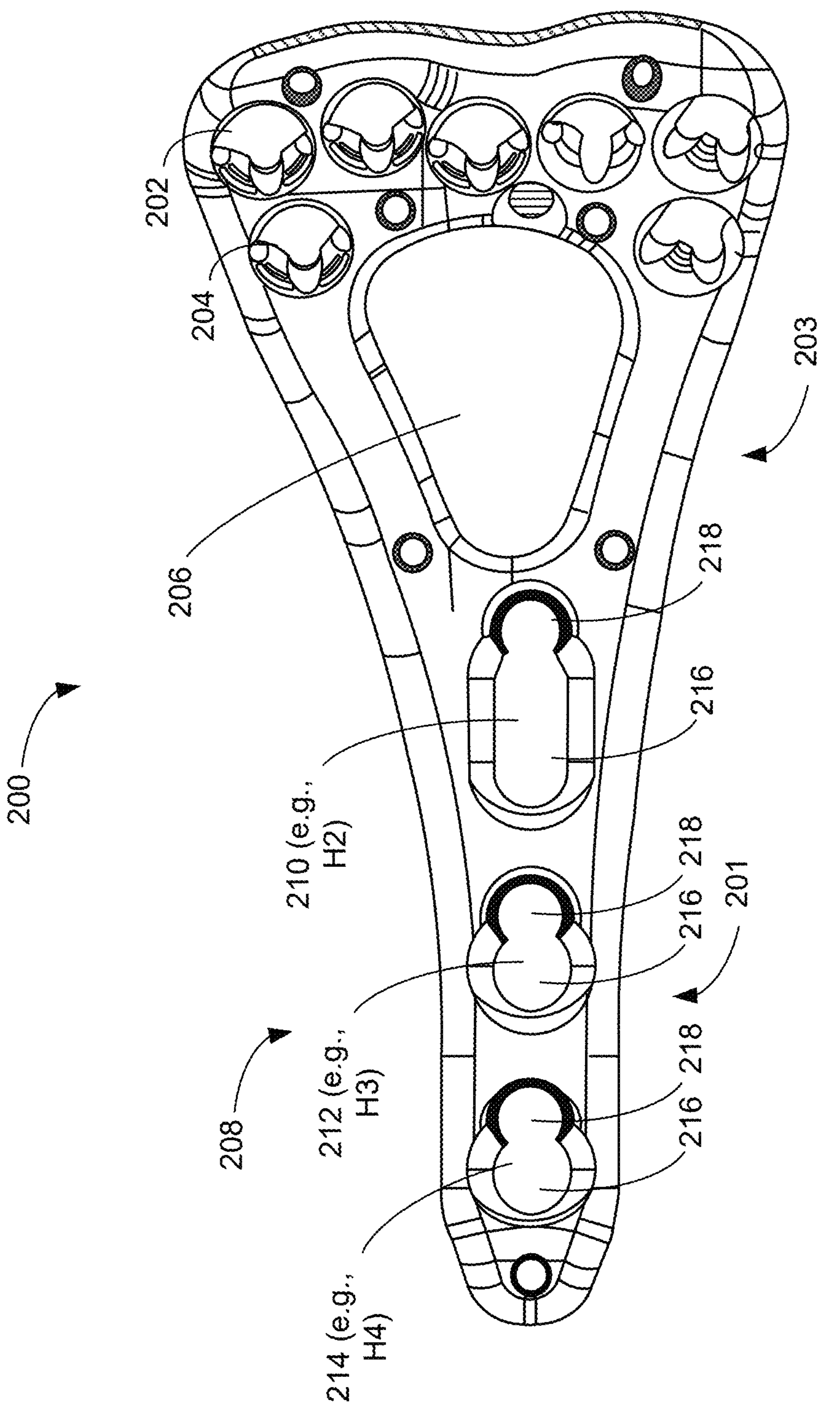
FIG. 2 is a view of an example bone fixation plate.
Figure 3:
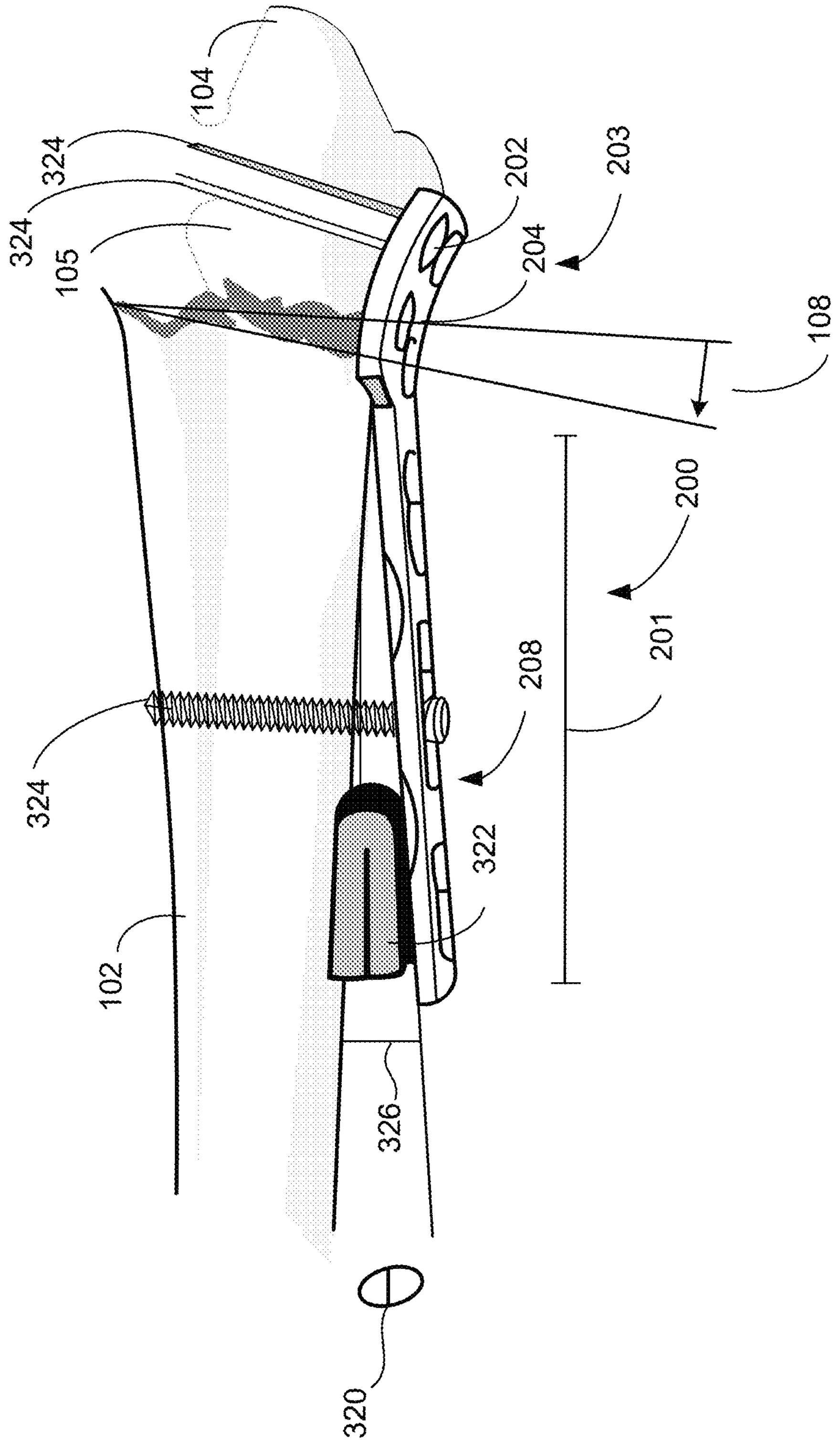
FIG. 3 is a view of the example joint of a patient of FIG. 1A with the example bone fixation plate of FIG. 2.

FIG. 2 is a view of an example bone fixation plate 200. FIG. 3 is a view of the example joint of a patient of FIG. 1A with the example bone fixation plate of FIG. 2. The bone fixation plate 200 includes one or more apertures in an elongated first portion 201. The one or more apertures may include a plurality of apertures, such as at least three apertures 210, 212, and 214. The three apertures may include an H2 aperture, an H3 aperture, and an H4 aperture, for example corresponding to a first aperture 210, a second aperture 212, and a third aperture 214 respectively. A distance, for example between the bone fixation plate 200 and a bone may be measured through the one or more of the apertures 210, 212, 214. Additionally, or alternatively, a fastener (e.g., screw) may be used to affix the bone fixation plate 200 to a surface, for example the bone 102. The one or more apertures 210, 212, 214 may be sized to accommodate different sized fasteners. The apertures are described further in U.S. Pat. No. 8,906,075B2 entitled "Methods and assemblies for aligning a bone fixation plate" and U.S. Pat. No. 9,370,386B2 entitled "Plating concept for distal radial fractures" both of which are hereby incorporated by reference.

An aperture, for example the first aperture 210, may include a first portion 216 and a second portion 218. The first portion may be elongated (e.g., longitudinally). The first portion may have a dimension, for example a transverse dimension, approximately equal to a fastener (e.g., the head of a screw). The aperture (e.g., 210) may include a second portion 218. The second portion 218 may be at least partially cylindrical. Additionally, or alternatively, the second portion 218 may include an opening continuous with an opening of the first portion 216. The second portion 218 may be threaded, for example with threading corresponding to threading of a fastener. A fastener may be disposed in the second portion 218 when in an affixed position (e.g., to a bone).

The bone fixation plate 200 may include a second portion 203. The second portion may include a first hole 202 and/or a second hole 204. The first hole 202 and/or the second hole 204 may be sized to receive a fastener (e.g., a screw). The fastener may affix the second portion 203 of the bone fixation plate 200 to a bone, for example the one or more carpals 105. The first hole 202 and/or the second hole 204 may be threaded, for example with threading corresponding to threading of a fastener. The second portion 203 may be connected to the first portion 201 at an angle, for example as in FIG. 3.

The second portion 203 may include a port 206. A user, for example a surgeon, may view the joint through the port 206. The user may view a fracture, for example a bone fracture line through the port 206 to aid in positioning of the bone fixation plate 200. One or more fasteners may be affixed to the one or more carpals 105 and/or the bone 102, through the first hole 202 and/or the second hole 204, for example to hold a relative position of the one or more carpals 105 and the bone fixation plate 200. One or more fasteners may (e.g., then) be affixed to the bone 102 through the one or more apertures 210, 212, 214, for example to hold a relative position of the bone 102 and the bone fixation plate 200. Additionally, or alternatively, a wire or a fastener may be used to take a measurement (e.g., distance and/or angle) from the bone fixation plate 200 to the bone 102, for example through the one or more apertures 210, 212, 214.

An operative procedure may include one or more of selection of a bone fixation plate, affixing the bone fixation plate, measuring a distance or angle, an osteotomy, a reaffixing or adjustment of the bone fixation plate, and/or removal of the bone fixation plate. A user (e.g., surgeon) may select a bone fixation plate, for example based on the patient and/or the injury. As shown in FIG. 3, the bone fixation plate 200 is affixed to the one or more carpals 105, for example using one or more fasteners 324. The fasteners may affix the bone fixation plate 200 to the one or more carpals 105 through the first hole 202 and/or the second hole 204. The first hole 202 may include a series of first holes. The second hole 204 may include a series of second holes. A user (e.g., surgeon) may determine to affix any number of fasteners 324 through any combination of first holes 202 and/or second holes 204.

A user may position the elongated first portion 201 of the bone fixation plate in a desired position. For example, the desired position may be such that the volar tilt angle 108 is approximately 10 degrees. The user may position and/or hold a position of the elongated first portion 201 of the bone fixation plate 200 by placing a spacer 322 between the elongated first portion 201 of the bone fixation plate 200 and the bone 102 (e.g., the radius). The user may select a spacer based on a desired size and shape, for example to achieve and/or maintain the desired volar tilt angle 108. For example, the user may select the spacer such that a desired distance 326 (e.g., between the elongated first portion 201 and the bone 102) and/or a desired angle 320 (e.g., between the elongated first portion 201 and the bone 102) is achieved and/or maintained. A user may (e.g., then) fasten the elongated first portion 201 to the bone 102 with one or more fasteners 324. For example, the fasteners may affix the elongated first portion 201 to the bone 102 through one or more of the apertures.

The user may (e.g., then) perform the osteotomy, for example while maintaining the desired volar tilt angle 108. If for example the volar tilt angle 108 is not at a desired value, the user may reaffix and/or adjust the bone fixation plate 200. The user may remove the bone fixation plate 200 by removing the fastener(s) 324, for example after the osteotomy is completed.

Figure 4A:
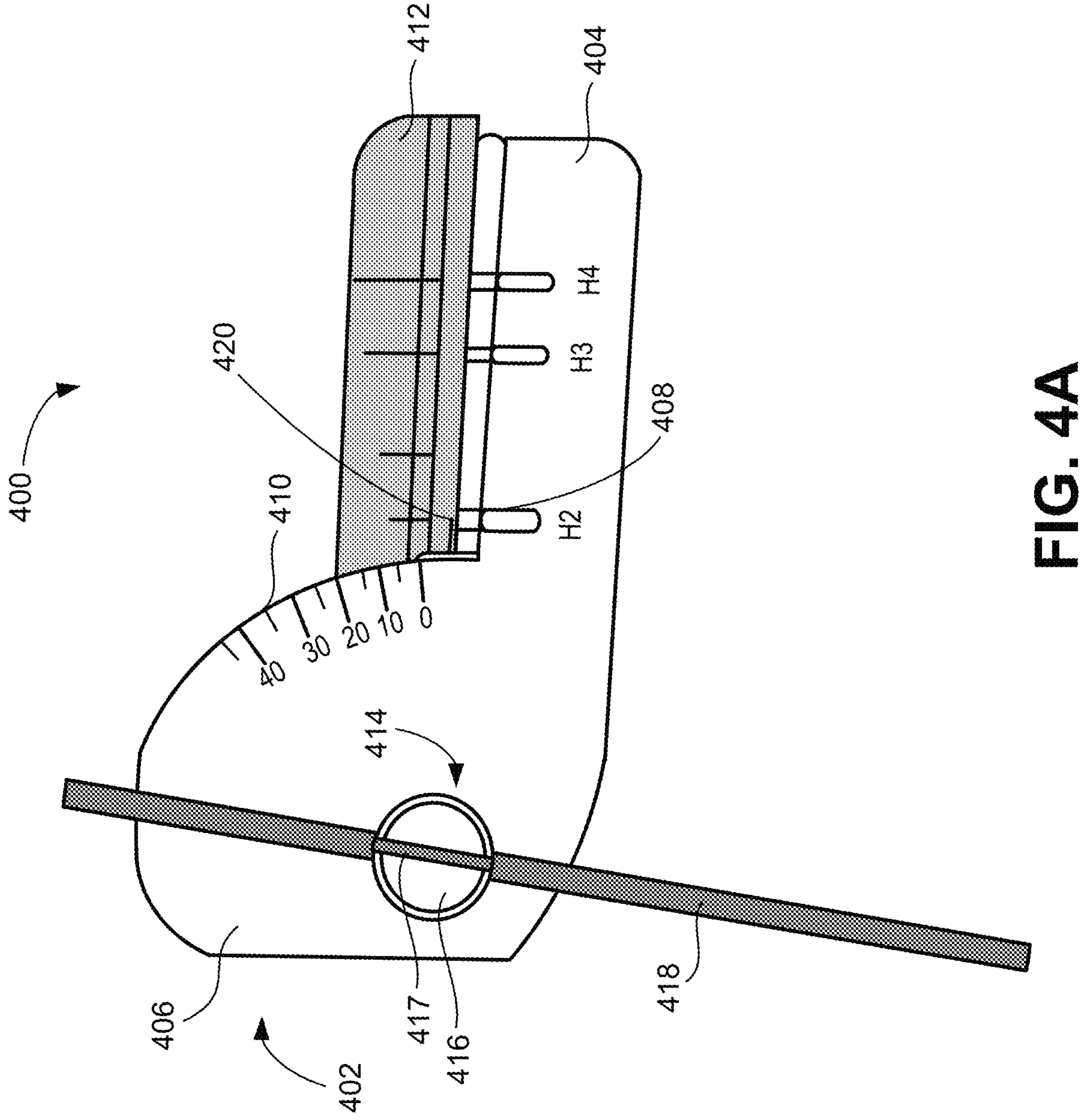
FIG. 4A is a view of an example device in a first position configured to convert an angle to a distance.

FIG. 4A is a view of an example device 400 in a first position configured to convert an angle to a distance. A user (e.g., surgeon) may utilize the distance for planning at least part of an operative procedure. For example, the user may utilize the determined distance to position a bone fixation plate for a corrective osteotomy. The device 400 may be configured to convert an angle to a distance. The device may include a body 402. The body 402 may include (e.g., define) an elongated first portion 404 and/or a second portion 406. The elongated first portion 404 may include at least one aperture 408. The at least one aperture 408 may be configured to receive a wire and/or a fastener (e.g., screw). The second portion may include angular indicia 410. For example, the angular indicia may include numerals. Each numeral may be associated with a hash mark. Hash marks may have differing lengths. For example, long hash marks may be associated with 0, 10, 20, 30, 40. Shorter hash marks may be associated with numerals ending in 5 (e.g., 5, 15, 25, 35, 45 etc.). Still shorter hash marks may be associated with other numerals, for example numerals ending in 1, 2, 3, 4, 6, 7, 8, and/or 9.

The device 400 may include an arm 412. The arm 412 may be rotatably coupled, for example to the body 402. Additionally, or alternatively, the arm 412 may be rotatably coupled at a rotation point 414. A knob 416 may be coupled to the body 402, for example at the rotation point 414. The device 400 may include a rod 418. For example, the rod 418 may be a Kirschner wire (k-wire). The rod 418 may be coupled to the arm 412, for example at the rotation point 414 and/or at the knob 416. The rod 414 may be removably coupled to the arm 412. For example, the rod 418 may be disposed in a channel positioned through the knob 416.

The rod 418 may be configured to rotate about the rotation point 414, for example with rotation of the arm 412. For example, a user (e.g., surgeon) may rotate the rod 418 about the rotation point 414 to a desired position. The knob 416 may rotate (e.g., about the rotation point 414) with rotation of the rod 418. The desired position of the rod 418 may correspond to the tangent line of the bone. The arm 412 may rotate (e.g., about the rotation point) with rotation of the rod 418 and/or of the knob 416. For example, the arm 412 may be rotated (e.g., by a user) by rotating the rod 416 and/or the knob. Additionally, or alternatively, the rod 418 may be omitted and a user may rotate the knob 416 directly. The knob 416 may include an indicator 417. For example, the indicator 417 may include a line. The indicator 417 may align with the tangent line when the arm 412 is in the first position.

The user may rotate the rod 418 into a desired position. For example, the user may rotate the rod 418 to a position corresponding to the tangent line. The arm 412 may be in the first position when the rod is in the position corresponding to the tangent line. The arm 412 may be in contact with the elongated first portion 404 in the first position.

The arm 412 may include a marker 420. The marker 420 may be configured to align with the angular indicia 410 of the second portion 406 of the body 402. For example, the marker may include a line. The line may point to the indicia 410, for example at a specific numeral and/or hash. The marker 420 may point to an indicia 410 indicating 0 degrees when the arm 412 is in the first position. The first position may correspond to a volar tilt angle of 10 degrees.

Figure 4B:
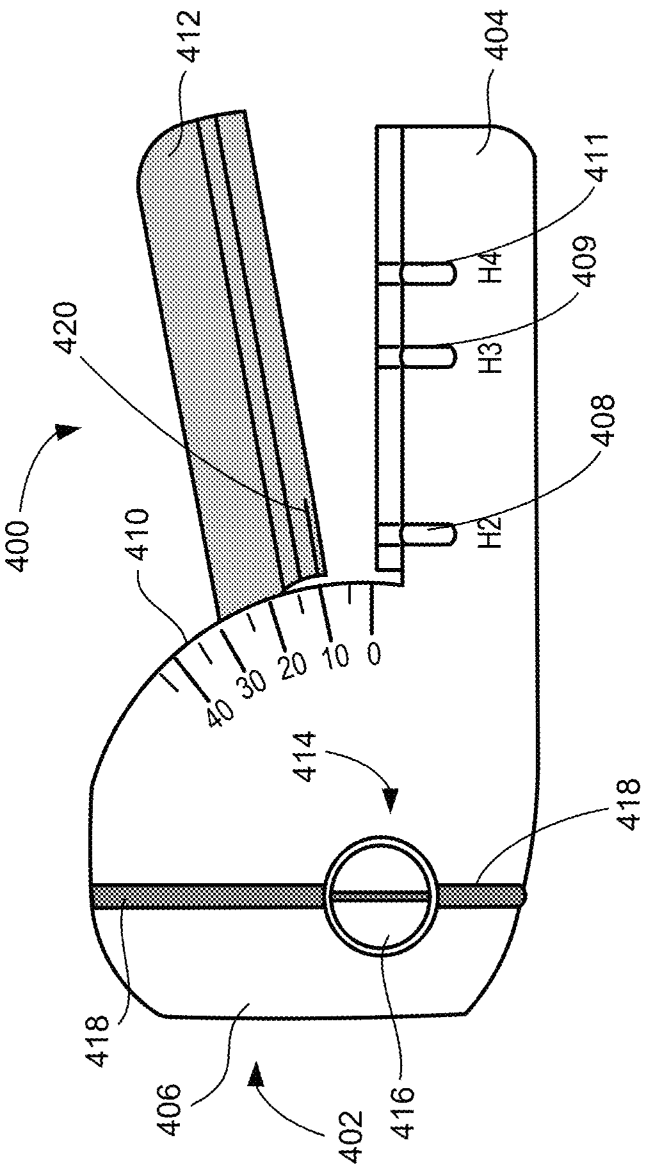
FIG. 4B is a view of the example device of FIG. 4A in a second position.

FIG. 4B is a view of the example device 400 of FIG. 4A in a second position. The user may rotate the rod 418 into a desired position. For example, the user may rotate the rod 418 to a position corresponding to the tangent line. The arm 412 may be in the second position when the rod and/or the knob 416 is in the position corresponding to the tangent line. For example, the arm 412 may not be in contact with the elongated first portion 404 in the second position.

The second position may correspond to a volar tilt angle of a value other than 10 degrees. For example, in FIG. 4B the marker 420 of the arm 412 points to an indicia 410 of 10 degrees. The indicia of 10 degrees corresponds to a needed correction of the volar tilt angle of 10 degrees. A user may measure a corrective distance using the indicia 420 angle. For example, a user may measure the corrective distance by inserting a wire or a fastener into one or more of the apertures 408, 409, 411 of the elongated first portion 404. Each of the apertures 408, 409, and 411 of the elongated first portion may respectively correspond to the apertures 210, 212, and 214 of the bone fixation plate. For example, a user may determine a corrective distance for the location of the H2 aperture (e.g., 210) by measuring the angle and/or distance between the elongated first portion 404 and the arm 412 at the H2 (e.g., 408) aperture of the device 400.

Figure 5A:
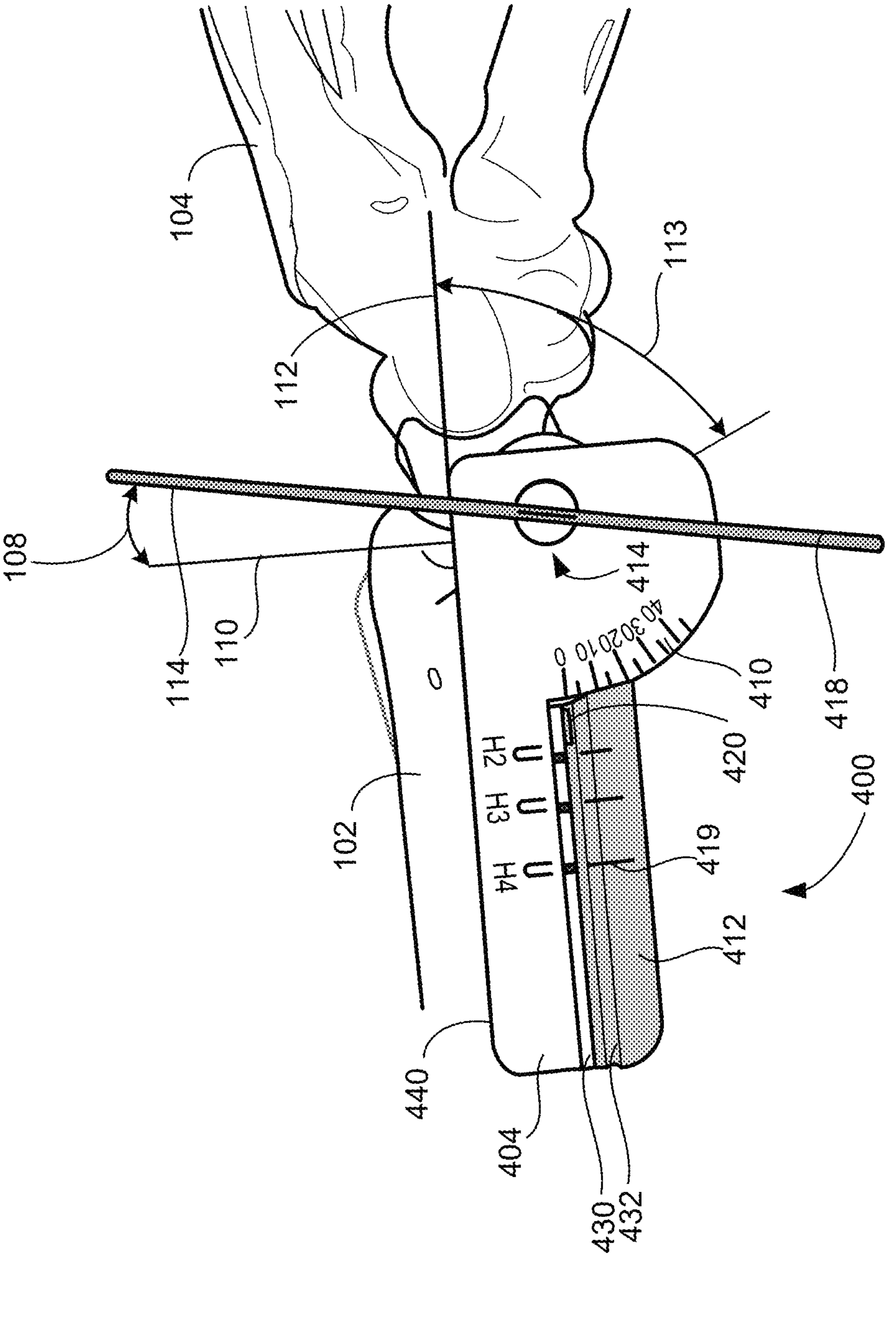
FIG. 5A is a view of the example device of FIG. 4A used to determine a volar tilt in the first position.

FIG. 5A is a view of the example device of FIG. 4A used to determine a volar tilt in the first position. The elongated first portion 404 of the device 400 may include a first lip 430. The at least one aperture may be disposed in the first lip. The arm 412 may comprise a second lip 432. The second lip 432 may be configured to abut a wire and/or a fastener. The at least one aperture may include at least three apertures. The three apertures may include the H2 aperture 408, an H3 aperture 409, and an H4 aperture 411.

The arm 412 may include one or more indicators 419. The one or more indicators may align with one or more apertures 408, 409, 411. For example, each of the one or more indicators 419 may align with a corresponding aperture 408, 409, 411. Additionally, or alternatively, the one or more indicators 419 may align with a wire when the wire is received in the (e.g., corresponding) aperture 408, 409, 411.

A user (e.g., surgeon) may rotate the rod 418 and/or the knob (e.g., about the rotation point 414) such that the rod 418 and/or knob aligns with the tangent line 114. For example, the user may rotate the rod 418 such that the rod 418 is tangent to the first point and the second point of the bone 102. In the first position the volar tilt angle is approximately 10 degrees. Additionally, in the first position the first lip 430 may be in contact with the second lip 432. The user may determine that no adjustment is needed in the first position. Additionally, or alternatively, the user may determine that correction is needed, for example if the volar tilt angle is not 10 degrees.

Additionally, the user may align an edge 440 of the device with the axis 112 of the bone 102. The edge 440 of the device 400 may be an edge 440 of the elongated first portion 404 of the device 400. The user may align the edge 440 to be parallel with the axis 112 of the bone, for example by abutting the edge 440 against the bone 112. The user may (e.g., then) rotate the rod 418 to be tangent to the first point 107 and the second point 109 of the bone 102. In the first position (e.g., when the indicia 410 and/or the marker 420) show that the there is no volar tilt angle correction needed (e.g., the indicia is 0), the user may determine that a corrective procedure is successful or unnecessary.

Figure 5B:
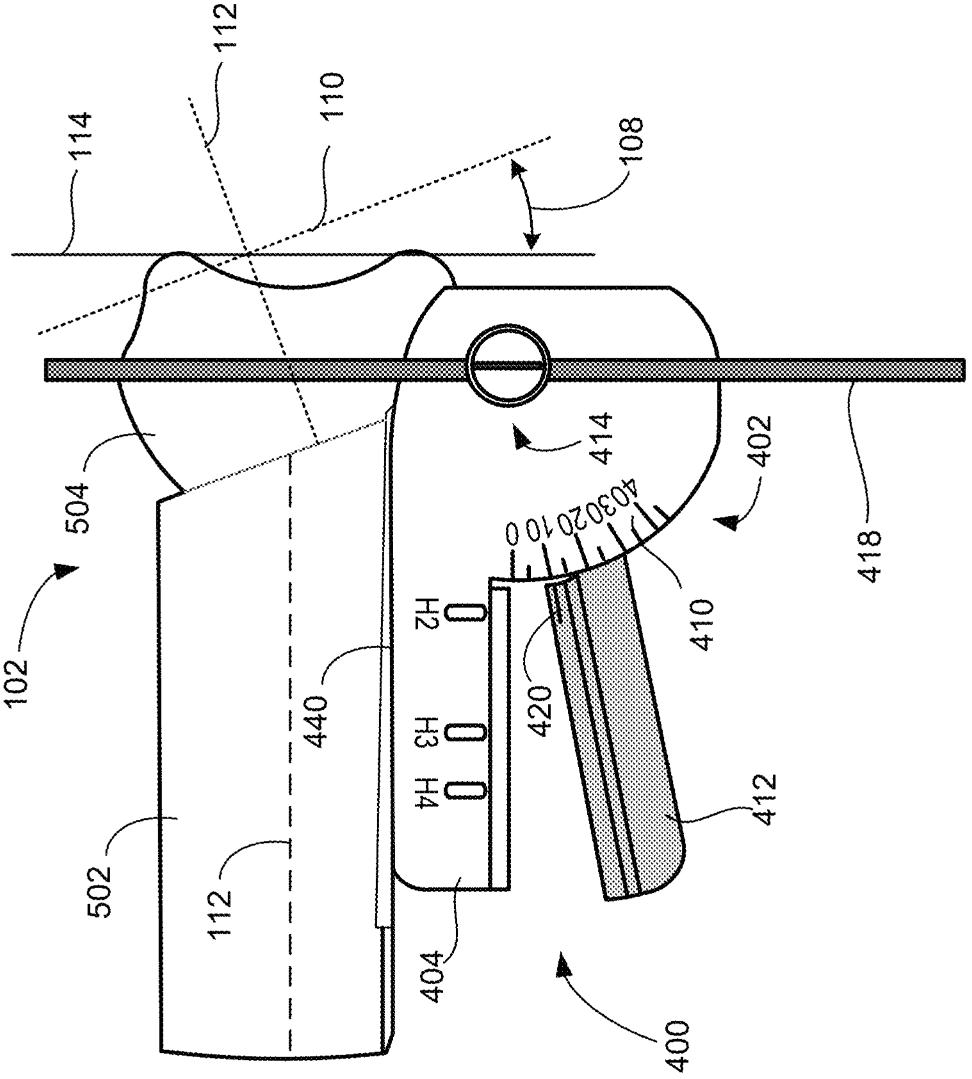
FIG. 5B is a view of the example device of FIG. 4A used to determine a volar tilt in the second position.

FIG. 5B is a view of the example device 400 of FIG. 4A used to determine a volar tilt angle in the second position. In FIG. 5B correction is needed. The arm 412 is not in contact with the elongated first portion 404. Additionally, marker 420 may point to an indicia 410 of 10 degrees. A user may place the device 400 along the bone 102, for example along the axis 112 (e.g., of a first portion 502 of the bone 102). The user may (e.g., then) rotate the rod 418.

FIG. 5B also shows a break or fracture of the bone 102. The axis 112 of a first portion 502 of the bone 102 is not aligned with the axis 112 of a second portion 504 of the bone 102. A user (e.g., surgeon) may rotate the rod 418 to a position corresponding to the tangent line 114 of the bone 102 (e.g., radius). The volar tilt angle 108 is the angle between the tangent line 114 (e.g., corresponding to the rod 418 position) and the line 110 perpendicular to the axis 112 of the second portion 504 of the bone. The user may measure the angle and/or distance, for example associated with one or more of the apertures in the elongated first portion 404, in order to determine the correction needed to restore the volar tilt angle to a desired value (e.g., 10 degrees).

The user may align the edge 440 of the device to be parallel with the axis 112 of the bone 102, for example by abutting the edge 440 against the bone 112. The user may align the device 400, for example the edge 440 of the device 400, with the first portion of the bone. The user may (e.g., then) rotate the rod 418 to be tangent to the first point and the second point of the bone 102, for example of the second portion 504 of the bone. When a volar tilt angle 108 correction is needed, the indicia 410 and or marker 420 will indicate a number other than 0. The indicia 410 and/or marker 420 may indicate the angle needed to restore the volar tilt angle 108 to the desired angle. For example, an indicia 410 of 10 degrees may correspond to a volar tilt angle 108 correction of 10 degrees.

The user may note the arm 412 position, for example the marker 420 position, when the rod 418 is parallel to (e.g., aligned with) the tangent line 114. The user may determine to perform an operative procedure to achieve a desired volar tilt angle 108 (e.g., of 10 degrees) based on the arm 412 position. The user may use a locking mechanism to keep the arm 412 stationary with respect to the body 402. Additionally, or alternatively, the user may record the indicia 410 value associated with the arm 412 (e.g., marker 420) position, for example after determining to perform an operative procedure. Locking mechanisms may include clamps or nuts for example. The coupling between arm 412 and body 402 can include a frictional drag so that the two parts are held against gravity and have some small resistance to moving with respect to each other to make the device 400 more user-friendly in a surgical setting. This can be achieved with a slight interference fit between arm 412 and body 402 or other known ways of providing some resistance to rotation.

Figure 6:
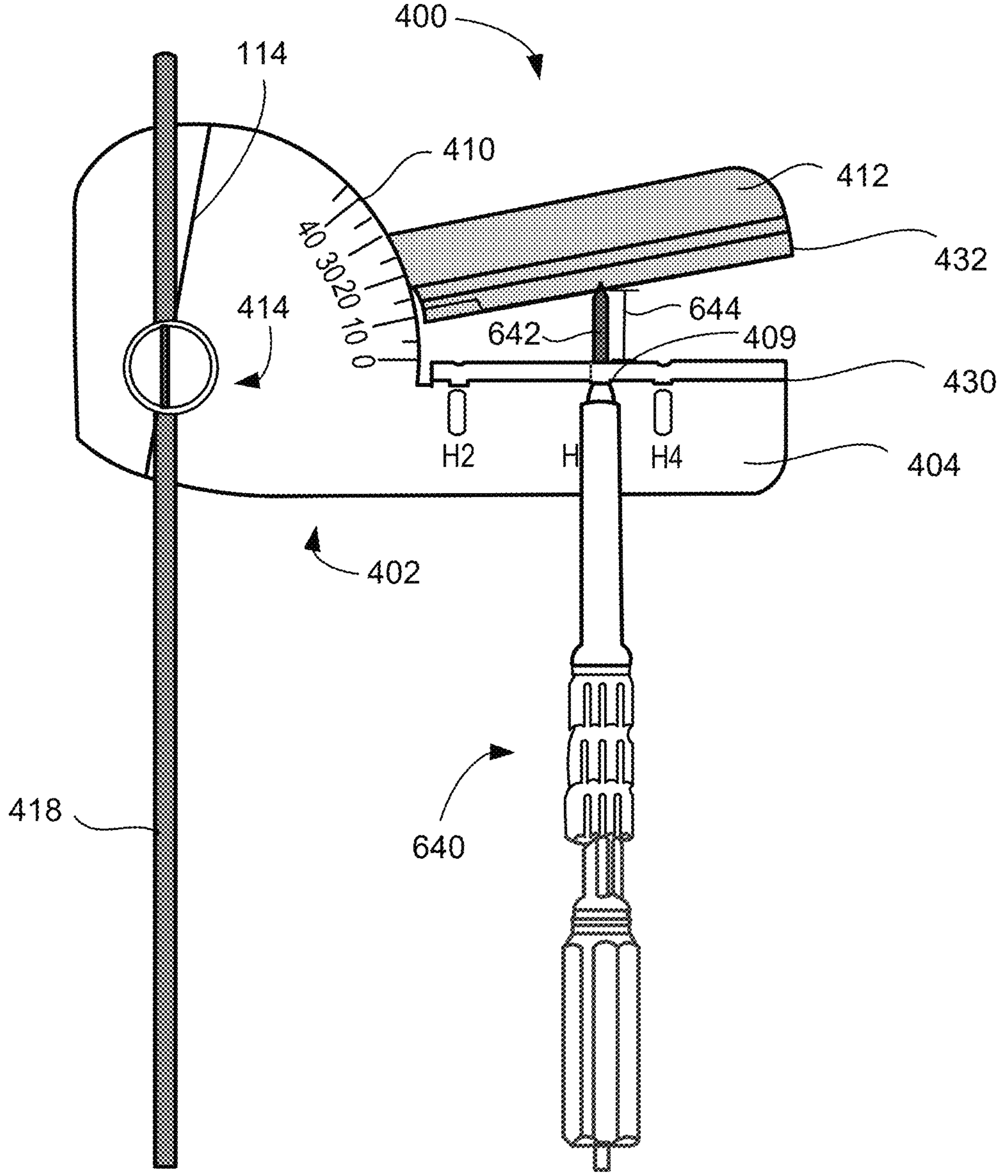
FIG. 6 is a view of the example device of FIG. 4A with an example distance holder.

FIG. 6 is a view of the example device 400 of FIG. 4A with an example distance holder 640. A user may determine that correction is needed, for example if the device is in the second position (e.g., the volar tilt is not 10 degrees). The user may insert the distance holder 640 into an aperture of the device 400, for example the H3 aperture 409. The tangent line 114 may be a physical line on the body 402 of the device 400. The tangent line 114 may be different, for example depending on the bone and/or the patient.

The distance holder 640 may include a wire 642. The wire 642 may extend from the aperture 409, for example in the lip 430, of the elongated first portion 404. The user may insert the distance holder 640 into the aperture 409 until the wire 642 contacts the arm 412, for example at the lip 432.

The user may use the indicia 410, for example that the user recorded (e.g., at FIG. 5B) to determine a distance 644. The user may (e.g., then) note the distance 644 of the wire 642 that extends between the elongated first portion 404 and the arm 412. The user may note the distance 644 (e.g., either) while the device 400 and/or distance holder 640 are positioned with the bone, and/or after the device 400 and/or distance holder 640 are removed from the patient. The distance holder 640 may include a locking mechanism, for example a clamping device as disclosed herein. The user may use distance holders 640 as disclosed herein to measure a distance, for example associated with the device 400. Additionally, or alternatively, the user may use a distance holder 640 to keep a bone fixation plate 200 and/or device 400 in place, for example during an operative procedure (e.g., for measurement and/or drilling/affixing).

The user may use the locking mechanism to lock the arm 412 in place with respect to the body 402. For example, the user may lock the arm 412 in place at the position corresponding to the determined volar tilt angle 108 for which correction is needed. Additionally, or alternatively, the user may record/note the position of the arm 412 and/or the associated indicia 410 value. The user may (e.g., then) insert the distance holder 640, for example a wire 642 of the distance holder 640, into the device. The user may insert the wire 642 into an aperture of the device 400. For example, the user may insert the wire 642 into aperture 409 until the wire 642 contacts the arm 412, for example at the lip 432.

The user may (e.g., then) note the distance 644 of the wire. For example, the user may note the distance 644 between the elongated first portion 404 (e.g., at first lip 430) and the arm 412 (e.g., at the second lip 432). The distance 644 may correspond to the value of the indicia 410 (e.g., for correction of the volar tilt angle). The user may lock the distance 644 of the wire 642, for example as disclosed herein. Additionally, or alternatively, the user may note the distance 644 of the wire 642, for example as disclosed herein.

Figure 7A:
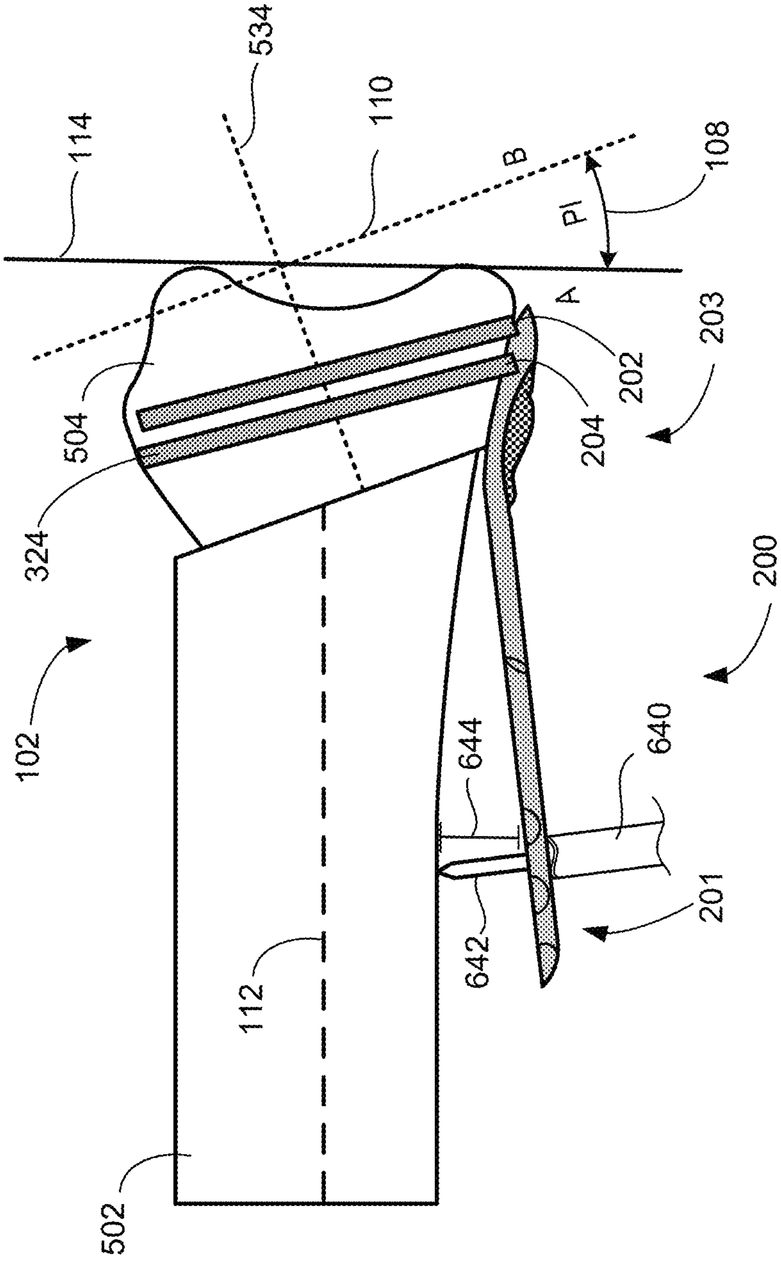
FIG. 7A is view of an example of a system including a bone fixation plate and a distance holder in a first position.

FIG. 7A is view of an example of a system including a bone fixation plate 200 and a distance holder 640 in a first position. FIG. 7A shows break or fracture of the bone 102. The axis 112 of a first portion 502 of the bone 102 is not aligned with the axis 112 of a second portion 504 of the bone 102. A user (e.g., surgeon) may determine the correction needed as discussed herein (e.g., with respect to FIG. 5B).

The user may insert the distance holder 640 into an aperture of the bone fixation plate 200, for example to hold the first portion 201 of the bone fixation plate 200 in place. The user may insert one or more fasteners 324 into the first hole 202 and/or a second hole 204 of the second portion 203 of the bone fixation plate. The user may (e.g., then) affix the bone fixation plate 200 to the bone 102, for example at the second portion 504 of the bone 102.

The user may insert the wire 642 of the distance holder 640 into the one or more apertures of the first portion 201 of the bone fixation plate 200 before or after affixing the bone fixation plate 200 to the bone 102, for example at the second portion 504 of the bone 102. The user may use the wire 642 for holding the bone fixation plate 200 in place and/or for determining a distance 644 of the wire 642.

The user may utilize the distance 644 of the wire 642 for correction, for example for a corrective open reduction and internal fixation alignment. The distance 644 may be the distance 644 determined (e.g., at FIG. 6). For example, the distance 644 may be the distance corresponding to the value of the indicia 410 (e.g., for correction of the volar tilt angle). The user may insert the wire 642 of the distance holder 640 into the bone fixation plate 200. The wire may abut against the bone 102, for example the first portion 502 of the bone 102. The user may use the distance holder 640 to keep the bone fixation plate 200 the distance 644 (e.g., determined distance from FIG. 6) from the bone 102 (e.g., the first portion 502 of the bone 102).

The distance holder 640 may maintain the distance 644 of the first portion 201 of the bone fixation plate 200 from the first portion 502 of the bone 102. For example, the user may utilize a clamping sleeve of the distance holder 640 to maintain the distance 644 of the wire 642. The user may (e.g., then) affix one or more fasteners 324, for example to affix a second portion 203 of the bone fixation plate 200 to the bone 102 at a second portion 504.

The user may insert the wire 642 into an aperture, for example a specific aperture, of the bone fixation plate 200. The (e.g., specific) aperture may correspond to the aperture of the device 400 used to determine the distance 644 (e.g., at FIG. 6). For example, the user may insert the wire 642 into the H3 aperture 212 of the bone fixation plate 200 corresponding to the H3 aperture 409 of the device 400 (e.g., used to determine the distance 644, for example at FIG. 6).

Figure 7B:
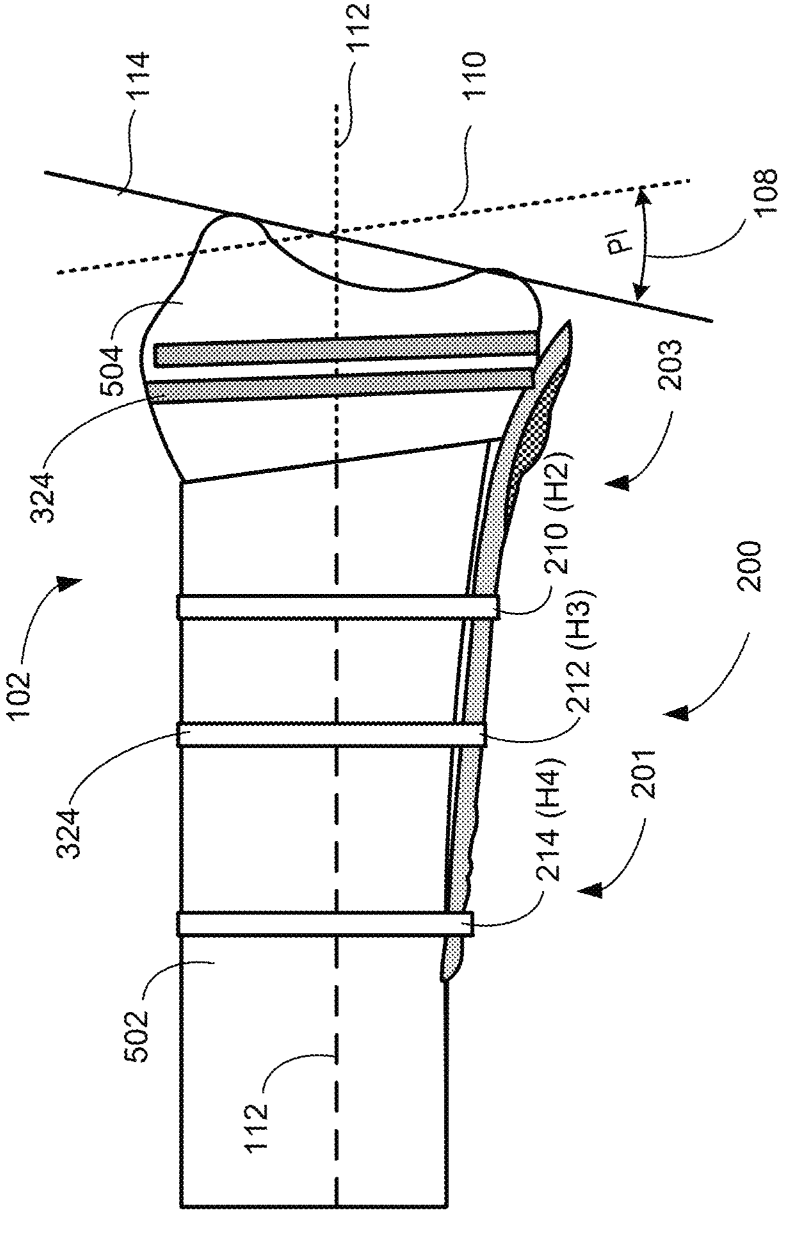
FIG. 7B is a view of an example of a system including the bone fixation plate and the distance holder of FIG. 7A in a second position.

FIG. 7B is view of an example of a system including the bone fixation plate 200 and the distance holder 640 of FIG. 7A in a second position. The user may affix one or more fasteners at the second portion 203 of the bone fixation plate 200, for example into the second portion 504 of the bone 102. The user may, for example after determining the correction needed to achieve the desired volar tilt angle 108 (e.g., as in the first position), affix one or more fasteners 324 at the first portion 201 of the bone fixation plate 200, for example into the first portion 502 of the bone (e.g., at FIG. 7A).

The axis 112 of the first portion 502 of the bone 102 may be aligned with the axis 112 of the second portion 504 of the bone 502, for example when the one or more fasteners 324 affix the first portion 201 of the bone fixation plate 200 to the first portion 502 of the bone 102. The user may achieve the desired volar tilt angle 108 (e.g., as in the first position) when the axis 112 of the first portion 502 of the bone 102 is aligned with the axis 112 of the second portion 504 of the bone 102. The user may affix one or more fasteners 324 to the bone fixation plate 200 and the bone 102 (e.g., the first portion 502 of the bone 102), for example through one or more apertures 210, 212, 214 of the bone fixation plate 200.

The user may achieve the desired volar tilt angle 108 (e.g., 10 degrees) by affixing the bone fixation plate 102 to the first portion 502 and the second portion 504 of the bone, which may align the axis 112 of the first portion 502 of the bone 102 with the axis 112 of the second portion 504 of the bone 102. The user may utilize the distance (e.g., 644 at FIG. 7A)

to achieve the desired volar tilt angle 108 and/or alignment of the axis 112 of the first portion 502 of the bone 102 with the axis 112 of the second portion 504 of the bone 102.

Figure 8A:
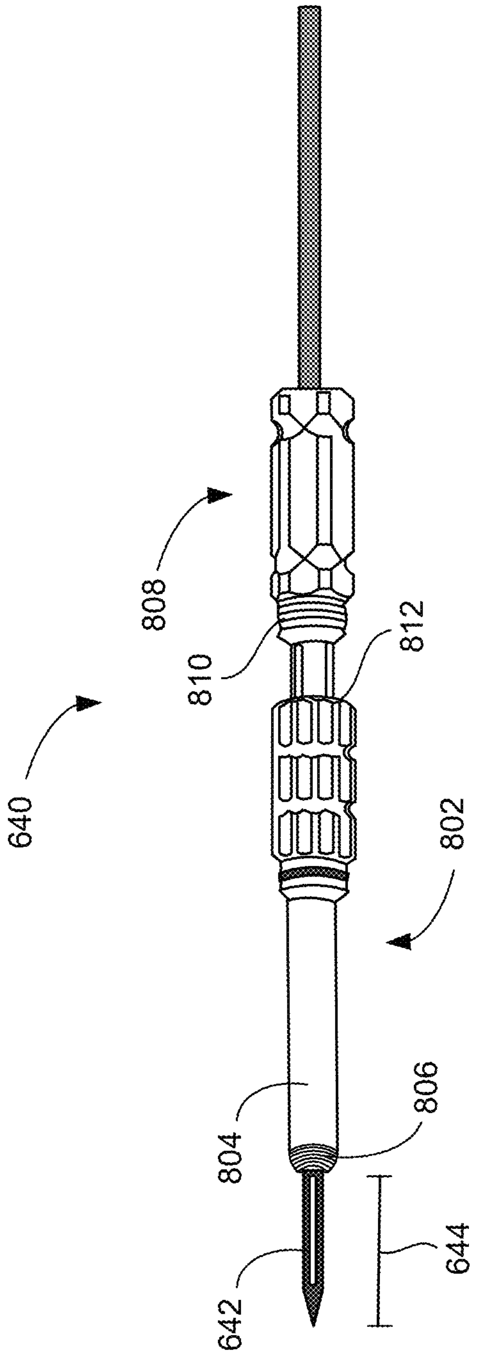
FIG. 8A is a view of an example distance holder with a clamping sleeve.

FIG. 8A is a view of an example distance holder 640 with a clamping sleeve 808. The distance holder 640 may include a guide tube 802. The guide tube 802 may define a hollow interior. The hollow interior may be configured to receive a wire 642, for example such that the wire 642 can extend through the guide tube 802. For example, the wire 642 may extend through the guide tube 802. The wire 642 may extend from the guide tube 802, for example from a tip 804 of the guide tube 802, by a distance 644. The tip 804 may include threading 806. The threading 806 may thread into corresponding threading of a bone fixation plate aperture (e.g., as in FIG. 7A), a bone fixation plate hole, and/or a device aperture (e.g., as in FIG. 6).

The distance holder 640 may include a clamping sleeve 808. The clamping sleeve 808 may be disposed around a circumference of the guide tube 802. The clamping sleeve 808 may be configured to receive the wire 642 and/or restrict motion of the wire 642 through the guide tube 802, for example when in a first configuration. The clamping sleeve 808 may be configured to allow movement of the wire 642 through the guide tube 802, for example when in a second configuration.

The clamping sleeve 808 may include threading 810. The threading may thread into corresponding threading 812 of the guide tube 802. A user (e.g., surgeon) may thread the clamping sleeve 808 and the guide tube 802 together, for example via threading 810 and threading 812, which may restrict the motion of the wire 642 (e.g., in the first configuration). For example, the user may tighten the threading 810 and threading 812 to restrict motion of the wire 642. The user may loosen the threading 810 and threading 812 to allow movement of the wire 642 through the guide tube 802 (e.g., in the second configuration). The user may loosen or tighten the connection (e.g., threading) of the guide tube 802 and clamping sleeve 808 when a desired length 644 of the wire 642 extends from the tip 804. Alternatively, or additionally, a user may connect the guide tube 802 and the clamping sleeve 808 with a snap fit and/or a quick connect/release (e.g., turn) mechanism.

Figure 8B:
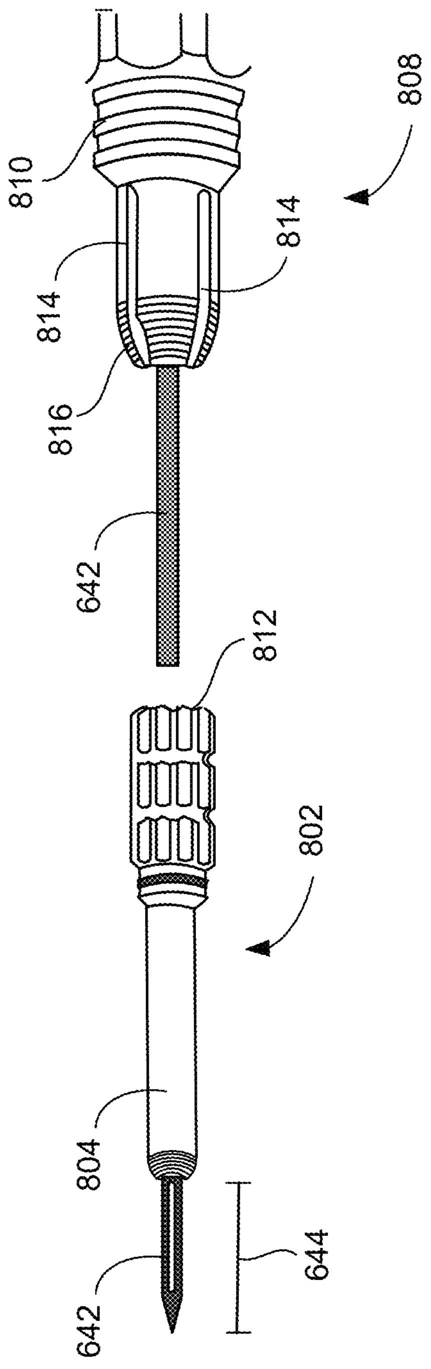

Additionally, or alternatively, the clamping sleeve 808 may include one or more flexible members. FIG. 8B shows an example clamping sleeve 808 and guide tube 802. The clamping sleeve 808 is not attached to the guide tube 802 in FIG. 8B for illustration purposes. The one or more flexible members 814 may extend from an end of the clamping sleeve 808 (e.g., and the elongated aperture).

The one or more flexible members 814 may contact the wire 642, for example when the clamping sleeve 808 is coupled to the guide tube 802. The one or more flexible members 814 may include (e.g., each include) threading 816, for example at a distal end (e.g., of the guide tube 808 and/or flexible member 814). The guide tube 808 may include threading 810, for example such that the clamping sleeve 808 may screw into the guide tube 802, for example at corresponding threading 812 of the guide tube 802. The one or more flexible members 814 may flex inward, for example to contact the wire 642 when the clamping sleeve 808 is screwed into the guide tube 802 (e.g., in the second configuration).

The one or more flexible members 814 may tighten around the wire 642 to restrict movement of the wire 642 through the guide tube 802 when a user tightens the connection (e.g., threading) of the guide tube 802 and clamping sleeve 808 (e.g., in the first configuration). The one or more flexible members 814 may loosen from around the wire 642 to allow movement of the wire 642 through the guide tube 802 when a user loosens the connection (e.g., threading) of the guide tube 802 and clamping sleeve 808 (e.g., in the second configuration). Additionally, or alternatively, the one or more flexible members 814 may tighten around the wire 642 at the clamping sleeve 808 moves further into the guide tube 802, for example toward the tip 804. The one or more flexible members 814 may loosen from around the wire 642 as the clamping sleeve 808 moves further out of the guide tube 802, for example away from the tip 804.

Figure 9:
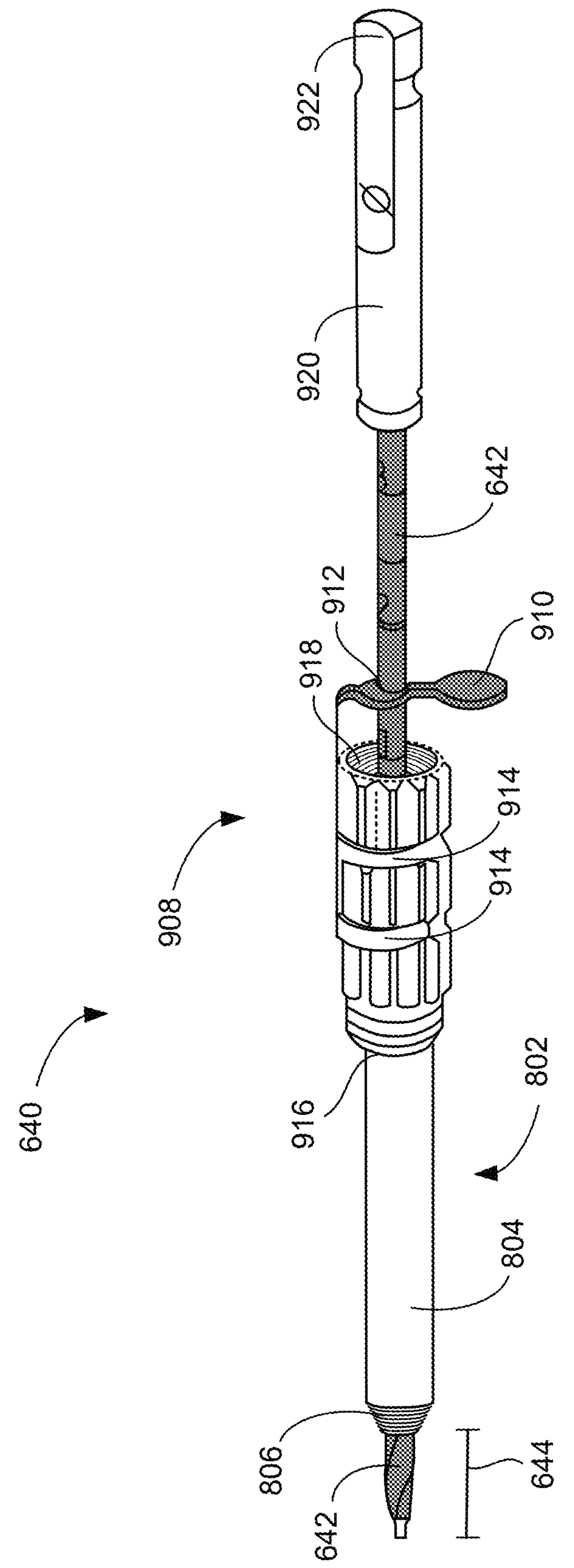
FIG. 9 is a view of an example distance holder with an example actuator.

FIG. 9 is a view of an example distance holder 640 with an example clamping sleeve 908. The clamping sleeve 908 may include an actuator 910. Additionally, or alternatively, the clamping sleeve 908 may include a hole 912. An interior surface of the hole 912 may contact the wire 642, for example when the wire 642 extends through the hole 912. The hole 912 may contact the wire to restrict the motion of the wire through the guide tube (e.g., in the first configuration).

The actuator 910 may be configured to be actuated to cause the hole 912 to separate from the wire 642. For example, a user may press the actuator 910 to separate the hold 912 from the wire 642 and allow movement of the wire 642 through the guide tube 802 (e.g., in the second configuration). The user may press the actuator 910 to cause the hole 912 to separate from the wire 642 and allow motion of the wire 642 until a desired length 644 of the wire 642 extends from the tip 804.

The actuator 910 and/or the hole 912 may be disposed in a plane, for example perpendicular to an axis associated with the motion of the wire 642 (e.g., the long axis of the wire). The clamping sleeve 908 may include one or more clips 914. The one or more clips 914 may at least partially enclose the guide tube 802. The clamping sleeve 908 may include an elongated aperture. The elongated aperture may receive the wire therethrough. The elongated aperture may include a first end 916 and a second end 918. The second end 918 may attach to the tip 804 of the guide tube 802, for example with threading.

The wire 642 may be a drill bit. For example, the drill bit may include a shank 920 and/or a tang 922. The shank 920 may fit into a drill, for example a chuck of the drill. The tang 922 may also fit into the drill, for example a spindle of the drill. The user may select a wire and/or drill bit based on one or more desired dimensions. The user may utilize the drill bit to trepan a hole, for example in a bone. Additionally, or alternatively, the user may utilize the drill bit to determine a length, for example the desired length 644 extending from the tip 804.

Figure 10:
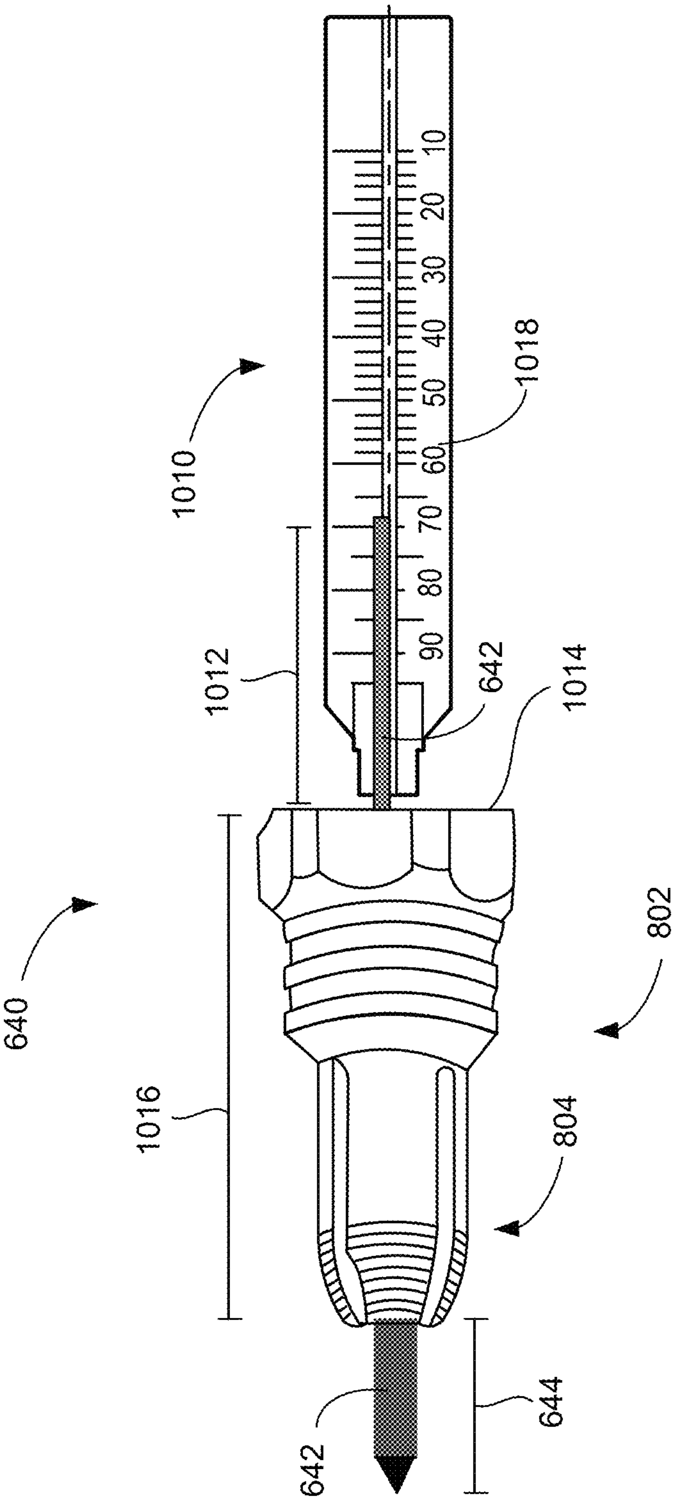
FIG. 10 is a view of an example distance holder with a measurement device.

The drill bit and/or wire 642 may include one or more markings, for example to determine a length. FIG. 10 is a view of an example distance holder 640 with a measurement device 1010. A user (e.g., surgeon) may insert the measurement device 1010 into the distance holder 640, for example at the guide tube 802 or a clamping sleeve. The wire 642 may have a predetermined distance. For example, the user may select a wire of a predetermined distance. The predetermined distance may be visible on (e.g., written on) the wire. The user may (e.g., then) determine the length 644 of the wire 642 extending from the guide tube 802 based on the predetermined distance and a second length 1012 of the wire 642. The second length 1012 of the wire 642 may be the length of wire protruding from the guide tube 802, for example from an end 1014 of the guide tube 802.

The user may determine the length 644 of the wire 642 extending from the tip 804 of the guide tube by subtracting the second length 1012 of the wire 642 protruding from the guide tube 802 and a third length 1016 of the guide tube 802 from the predetermined distance (e.g., of the entire wire). The user may view the measurement device 1010 to determine the second length 1012. For example, the user may view a marking 1018 on the measurement device 1010. The markings 1018 may be similar to the indicia disclosed herein. For example, the markings 1018 may include numerals. Each numeral may be associated with a hash mark. Hash marks may have differing lengths. For example, long hash marks may be associated with 0, 10, 20, 30, 40, 50, 60, 70, 80, and/or 90. Shorter hash marks may be associated with numerals ending in 5 (e.g., 5, 15, 25, etc.). Still shorter hash marks may be associated with other numerals, for example numerals ending in 1, 2, 3, 4, 6, 7, 8, and/or 9.

Figure 11:
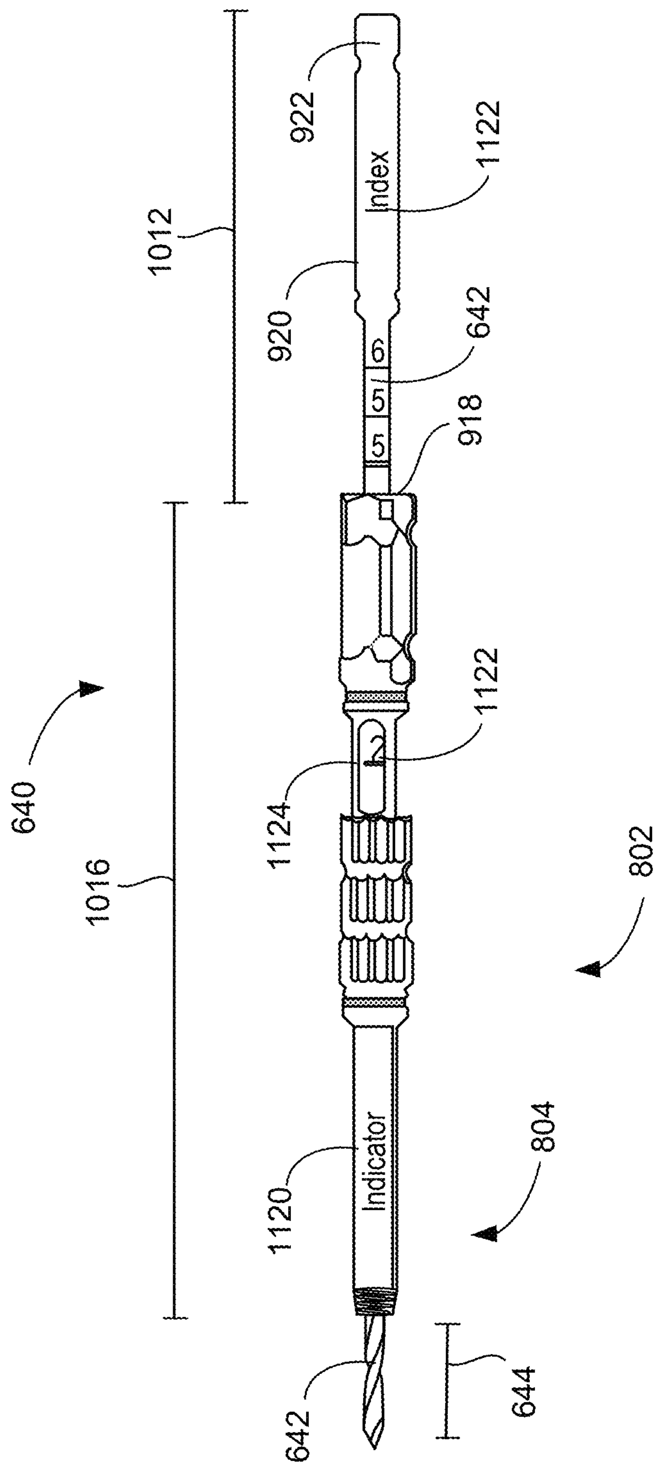
FIG. 11 is a view of another example distance holder with a measurement device.

FIG. 11 is a view of another example distance holder 640 with a measurement system. A user may determine the length 644 of the wire 642 or drill bit extending from the tip 804 of the guide tube 802, for example using one or more indicators. There may be a guide tube indicator 1120 on the guide tube 802, for example at the tip 804 of the guide tube 802. The guide tube indicator 1120 may include a length of the guide tube 802 (e.g., the third length 1016).

Additionally, or alternatively, there may be a drill bit indicator 1122, for example on the wire 642 or drill bit. The drill bit indicator 1122 may include a length of the drill bit protruding from the guide tube 802, for example at the second end 918. The drill bit indicator 1122 may include numerals and/or hash marks as disclosed herein and/or an index. The index may be an alpha numeric index. The index may correspond to one or more dimensions (e.g., the third length 1016). A user (e.g., surgeon) may determine the one or more dimensions based on the index, for example using a lookup table.

The distance holder 640 may include a window 1124, for example at the guide tube 802. A user may view the drill bit indicator 1122 through the window 1124. The user may use the drill bit indicator 1122 in the window 1124 to determine the length 644 of the wire or drill bit extending from the tip 804 of the guide tube 802, for example using a lookup table (e.g., as in FIG. 13). The drill bit indicator 1122 may additionally, or alternatively, include one or more numbers that may be visible to a user. For example, a number of the drill bit indicator 1122 may be visible through the window 1124.

Figure 12:
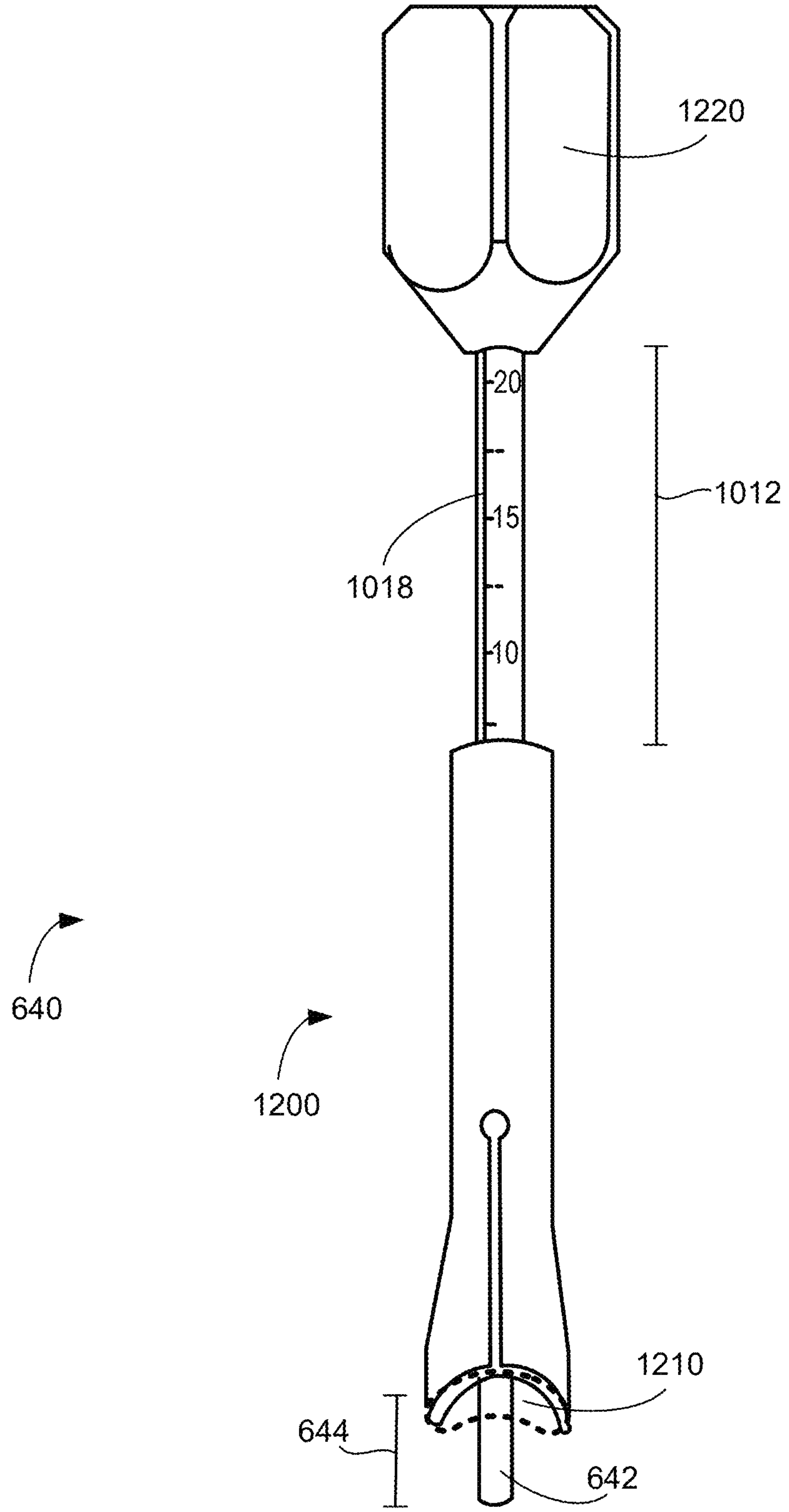
FIG. 12 is a view of an example measurement device with a clip.

FIG. 12 is a view of an example distance holder 640 with a post 1200. A user may insert the post 1200 onto a bone fixation plate, for example at a hole or aperture of the bone fixation plate. A wire 642 may extend from a connector 1210 of the post 1200, for example by a length 644. The user may view the post 1200 to determine a second length 1012. For example, the user may view a marking 1018 on the distance holder 640, for example on the post 1200. The markings 1018 may be similar to the indicia disclosed herein.

The connector 1210 may attach to a bone fixation plate (e.g., at a hole or aperture). For example, the connector may attach to the bone fixation plate with a snap fit. Alternatively, or additionally, the connector 1210 may attach to the bone fixation plate with a quick connect/release (e.g., turn) mechanism, for example a half-turn or quarter-turn release. The user may turn a handle 1220, for example to activate the quick connect/release mechanism. Additionally, or alternatively, the user may use the handle 1220 to position the post 1200 and/or the distance holder 640.

Figure 13:
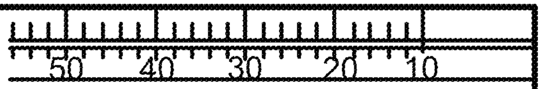
FIG. 13 is an example conversion table.

FIG. 13 is an example conversion table 1300. The conversion table 1300 includes an angle, for example the angle indicated by indicia (e.g., as in FIG. 4B) of a device, such as the device 400. The angle may be used to determine a corrective distance relative to one or more holes within the device (e.g., the device 400). The corrective distance may correspond to a distance a wire and/or a drill bit extends from a guide tube (e.g., at 644 in FIG. 8A). Additionally, or alternatively, the angle may correspond to a corrective distance for one or more apertures. The one or more apertures may be one or more apertures in a device, for example one or more of an H2 aperture 408, an H3 aperture 409, and/or an H4 aperture 411 as in FIG. 4B. Additionally, or alternatively, the one or more apertures may be one or more apertures in a bone fixation plate, for example one or more of an H2 aperture 210, an H3 aperture 212, and/or an H4 aperture 214 as in FIG. 2.

A user may use the conversion table 1300 to determine the corrective distance, for example for a particular aperture, associated with the angle (e.g., indicated on the device 400). Additionally, or alternatively, the user may determine the corrective distance for a particular plate (e.g., bone fixation plate) and/or device, for example one or more of A and/or B. The user may use a distance holder 640 to keep a bone fixation plate 200 and/or device 400 in place, for example at the determined corrective distance. For example, the user may set the length 644 of the wire and/or drill bit to the determined corrective distance (e.g., from the conversion table 1300). The bone fixation plate 200 and/or device 400 may include a fourth aperture (not shown). The fourth aperture may correspond to an H1 aperture, which may correspond to Hole 1 of the conversion table 1300.

In Example 1, a device comprises a guide tube that defines a hollow interior configured to receive a wire such that the wire can extend through the guide tube. The device comprises a clamping sleeve disposed around a circumference of the guide tube. The clamping sleeve is configured to receive the wire and restrict motion of the wire through the guide tube when in a first configuration. The clamping sleeve is configured to allow movement of the wire through the guide tube when in a second configuration.

In Example 2, the clamping sleeve of the device of Example 1 comprises a hole and an actuator. An interior surface of the hole is configured to contact the wire when the wire is extending through the hole to restrict the motion of the wire through the guide tube when in the first configuration. The actuator is configured to be actuated to cause the hole to separate from the wire to allow movement of the wire through the guide tube when in the second configuration.

In Example 3, the actuator and the hole of the device of Example 2 are comprised in a plane perpendicular to an axis associated with the motion of the wire. The clamping sleeve further comprises at least one clip configured to at least partially enclose the guide tube.

In Example 4, the clamping sleeve of the device of Example 1 comprises an elongated aperture configured to receive the wire therethrough. The elongated aperture comprises a first end and a second end. The clamping sleeve comprises a plurality of flexible members that extend from the second end of the elongated aperture. The plurality of flexible members are configured to contact the wire when the clamping sleeve is coupled to the guide tube.

In Example 5, the plurality of flexible members of the device of Example 4 comprise threading at a distal end. The guide tube comprises threading such that the clamping sleeve is configured to screw into the guide tube. The plurality of flexible members are configured to flex inward to contact the wire when the clamping sleeve is screwed into the guide tube in the second configuration.

In Example 6, the guide tube of the device of Example 1 comprises threading such that the guide tube is configured to thread into a bone fixation bone fixation plate.

In Example 7, the guide tube of the device of Example 1 comprises a window configured to display a value indicative of a length of the wire extending from an end of the guide tube.

What is claimed is:

1. A device used to assist in a medical procedure, the device configured to convert an angle to a distance, the device comprising:

a body defining an elongated first portion and a second portion, wherein the elongated first portion comprises at least one aperture configured to receive a wire, and wherein the second portion comprises angular indicia;

an arm rotatably coupled to the body at a rotation point; and a rod coupled to the arm at the rotation point, wherein the rod is configured to rotate about the rotation point with rotation of the arm, and wherein, when the rod is aligned to be parallel with a plane, the arm is configured to align with an angular indicia of the second portion of the body to indicate an angle, and the arm is configured to indicate a distance to the at least one aperture of the elongated first portion of the body.

2. The device of claim 1, wherein the distance indicates a depth of a screw for screwing a plate onto a wrist of a patient or a depth that the wire can extend through the aperture when the wire is used to position a bone fixation plate for screwing onto the wrist of the patient.

3. The device of claim 2, wherein the distance is associated with a corrective open reduction and internal fixation alignment.

4. The device of claim 1, wherein the plane comprises a tangent line drawn along a slope of a dorsal-to-palmar surface of a wrist of a patient.

5. The device of claim 4, wherein the second portion comprises a line corresponding to the tangent line drawn along the slope of the dorsal-to-palmar surface of the wrist of a patient.

6. The device of claim 1, wherein the arm comprises a marker that is configured to align with the angular indicia of the second portion of the body.

7. The device of claim 1, wherein the elongated first portion comprises a first lip, the at least one aperture is comprised in the first lip, and the arm comprises a second lip configured to abut the wire.

8. The device of claim 1, wherein the at least one aperture comprises at least three apertures, the at least three apertures comprising an H2 aperture, an H3 aperture, and an H4 aperture, and wherein each of the at least three apertures corresponds to a respective aperture on a bone fixation plate.

9. The device of claim 1, wherein the angular indicia indicates a value of zero when the arm is in contact with the elongated first portion.

10. The device of claim 9, wherein the angular indicia indicating the value of zero and the arm in contact with the elongated first portion comprises a first position of the device, wherein the first position of the device corresponds to a volar tilt angle of ten degrees.

11. The device of claim 10, further comprising a knob disposed at the rotation point and a channel positioned through the knob, wherein the rod is coupled to the arm at the rotation point through the channel.

12. The device of claim 11, wherein the knob comprises an indicator configured to align with a tangent line drawn along a slope of a dorsal-to-palmar surface of a wrist of a patient when the device is in the first position.

13. The device of claim 1, wherein the elongated first portion comprises a straight edge configured to abut against a bone, the straight edge disposed distal to the arm during the procedure.

14. The device of claim 1, comprising a locking mechanism configured to keep the arm stationary with respect to the body.

15. The device of claim 1, wherein the wire comprises a k-wire and the at least one aperture comprises a circumference configured to accommodate the k-wire when the k-wire is received in the aperture.

16. The device of claim 1, wherein the arm comprises at least one indicator associated with the at least one aperture, the at least one indicator configured to align with the at least one aperture and the wire when the wire is received in the aperture.

17. The device of claim 1, wherein the arm is configured to indicate the distance to the at least one aperture of the elongated first portion of the body as a distance between the arm and the elongated first portion at a position corresponding to the at least one aperture.

18. A system comprising:

a bone fixation plate;

a distance holder device comprising:

a guide tube that defines a hollow interior configured to receive a wire such that the wire can extend through the guide tube; and a clamping sleeve disposed around a circumference of the guide tube, wherein the clamping sleeve is configured to receive the wire and restrict motion of the wire through the guide tube when in a first configuration, and wherein the clamping sleeve is configured to allow movement of the wire through the guide tube when in a second configuration; and a device configured to convert an angle to a distance, wherein the device comprises:

a body defining an elongated first portion and a second portion, wherein the elongated first portion comprises at least one aperture configured to receive the wire, and wherein the second portion comprises angular indicia;

an arm rotatably coupled to the body at a rotation point; and a rod coupled to the arm at the rotation point, wherein the rod is configured to rotate about the rotation point with rotation of the arm, wherein, when the rod is aligned to be parallel with a plane, the arm is configured to align with an angular indicia of the second portion of the body to indicate an angle, and the arm is configured to indicate a distance to the at least one aperture of the elongated first portion of the body.

19. The system of claim 18, wherein the bone fixation plate comprises a plurality of apertures, and wherein the wire is configured to extend through the hollow interior of the distance holder device and through an aperture of the bone fixation plate to support the bone fixation plate when securing the bone fixation plate to a patient.

20. The system of claim 19, wherein the distance indicated by the arm indicates a distance that the wire should extend out of a distal end of the guide tube when the distance holder device is supporting the bone fixation plate when securing the bone fixation plate to the patient.

* * * * *